United States Patent [19]

Brockemeyer et al.

[11] 3,970,750
[45] July 20, 1976

[54] EFFERVESCENT POTASSIUM CHLORIDE COMPOSITION

[75] Inventors: Eugene W. Brockemeyer, Lincoln, Nebr.; Michael B. Rodell, Santa Ana, Calif.

[73] Assignee: Sandoz, Inc., E. Hanover, N.J.

[22] Filed: May 30, 1975

[21] Appl. No.: 582,130

Related U.S. Application Data

[63] Continuation-in-part of Ser. No. 513,041, Oct. 8, 1974, abandoned, which is a continuation-in-part of Ser. No. 358,662, May 9, 1973, abandoned, which is a continuation-in-part of Ser. No. 192,632, Oct. 26, 1971, abandoned.

[52] U.S. Cl. .............................. 424/153; 424/127; 424/319
[51] Int. Cl.² ............... A61K 31/14; A61K 31/195; A61K 33/00
[58] Field of Search ........... 424/128, 153, 154, 156, 424/127

[56] References Cited
UNITED STATES PATENTS

| | | | |
|---|---|---|---|
| 2,101,867 | 12/1937 | Miller et al. | 424/233 |
| 3,337,404 | 8/1967 | Polli et al. | 424/153 |
| 3,822,344 | 7/1974 | Corker | 424/319 |

*Primary Examiner*—Stanley J. Friedman
*Attorney, Agent, or Firm*—Gerald D. Sharkin; Robert S. Honor; Thomas O. McGovern

[57] ABSTRACT

A method of administering large dosages of potassium and chloride ions in an effervescent drink, wherein the ratio of potassium ion to chloride is maintained in a ratio of 1 to 1 with hydrochloride salts of basic amino acids.

22 Claims, No Drawings

EFFERVESCENT POTASSIUM CHLORIDE COMPOSITION

This application is a continuation-in-part of copending application, Ser. No. 513,041, filed Oct. 8, 1974, now abandoned, which in turn is a continuation-in-part of copending U.S. Pat. application, Ser. No. 358,662, filed May 9, 1973, now abandoned, which in turn is a continuation-in-part of then copending U.S. Pat. application, Ser. No. 192,632, filed Oct. 26, 1971, now abandoned.

This invention relates to a method of administering large doses of potassium and chloride ion in the form of a pleasant tasting effervescent drink, wherein the ratio of potassium ion to chloride ion is maintained in a ratio of 1 to 1.

The invention also relates to a stable effervescent composition containing potassium chloride which forms, on addition to water, a pleasant tasting drink in which the ratio of potassium ion to chloride ion is 1 to 1.

Normally, in the treatment of potassium depletion (hypokalemia), it is customary to administer potassium chloride in the form of tablets containing up to 500 milligrams of the salt. Where larger amounts of potassium chloride are to be administered, it is generally done intravenously using dilute solutions of the salt so as to avoid a sudden increase in blood plasma potassium, which could be fatal. Intravenous administration is, of course, much less desirable than oral administration; but tablets containing large amounts of potassium chloride are difficult to administer because of the size and unpleasant taste, which also renders multiple administration objectionable. Any effort made to improve the taste of such tablets in the usual manner with flavoring and sweeteners results in tablets even larger and more difficult to administer conveniently.

In attempting to solve the problem, it has been found that effervescent drinks containing the desired high levels of potassium chloride do provide a pleasant tasting method for administering the salt. The effervescence is normally produced by the reaction of potassium rather than sodium carbonate and an organic acid, since potassium chloride is usually administered in a regimen free of sodium. However, the extra potassium ion introduced into the drink by the reaction of the potassium carbonates and organic acid in the effervescent formulation upsets the 1 to 1 ratio of potassium ion and chloride ion in the drink. This is highly undesirable because potassium depletion is most frequently associated with hypochloremia and alkalosis, a state which very often results from treatment with potent kaliuretic diuretics. When hypochloremic alkalosis is present, the administration of potassium ion without balancing chloride ion will only worsen the potassium depletion, as the increased alkalosis results in greater movement of potassium ion into the cells thereby enhancing the secretion of potassium ion.

Potassium depletion can only be repaired when the body's chlorine stores are at the normal level; and when hypochloremia and alkalosis are present, this cannot be accomplished unless there is a 1 to 1 ratio of potassium ion to chloride ion in the preparation used to treat the potassium depletion.

One of the methods proposed for treating hypokalemia where hypochloremia is present, is described in U.S. Pat. No. 3,708,574, issued Jan. 2, 1973. In the composition disclosed by this Patent, the potassium chloride is generated in situ from potassium bicarbonate and an acidic amino acid hydrochloride, such as glycine hydrochloride or betaine hydrochloride. Theoretically, the effervescent solution produced with this composition should contain potassium and chloride ions in a 1 to 1 ratio. However, the dry composition has poor stability properties, which result in a decrease of effervescent capacity on storage with a consequent loss of palatability and taste characteristics.

The present invention, accordingly, provides a method of orally administering large quantities of potassium and chloride ions in a 1 to 1 ratio, which comprises administering the ions in a palatable effervescent drink resulting from the dissolution in water of a stable composition, i.e., a composition which is stable on storage over long periods, in unit dosage form comprising from 500 to 1,500 milligrams of potassium chloride, 500 to 2,000 milligrams of potassium carbonate or bicarbonate, 500 to 2,000 milligrams of a substance which on dissolution in water forms an acid reacting solution, and a quantity of a hydrochloride salt of a basic amino acid sufficient to provide one chloride ion for each potassium ion liberated by the dissolution of the composition in water.

The present invention also provides a method of treating potassium depletion which comprises orally administering to a human being in need of said treatment large doses of potassium chloride in a pleasant tasting effervescent drink resulting from the dissolution in water of a stable composition in unit dosage form comprising from 500 to 1,500 milligrams of potassium chloride, 500 to 2,000 milligrams of potassium carbonate or bicarbonate, 500 to 2,000 milligrams of a substance which on dissolution in water forms an acid reacting solution and a quantity of a hydrochloride salt of a basic amino acid sufficient to provide one chloride ion for each potassium ion liberated by the dissolution of the composition in water.

The present invention further provides a stable effervescent potassium chloride composition for oral administration in a palatable effervescent drink form comprising, in unit form, 500 to 1,500 milligrams of potassium chloride, 500 to 2,000 milligrams of potassium carbonate or bicarbonate, 500 to 2,000 milligrams of a substance which on dissolution in water forms an acid reacting solution, and a quantity of a hydrochloride salt of a basic amino acid sufficient to provide one chloride ion for each potassium ion present in the potassium carbonate or bicarbonate.

The stable composition of this invention, when dissolved in water, provides a pleasant tasting effervescent drink in which the ratio of potassium ion to chloride ion is 1 to 1. The desired taste characteristics and balance between potassium ion and chloride ion, it has been discovered, can be provided by including in the potassium chloride effervescent composition a sufficient quantity of a basic amino acid hydrochloride to provide an amount of chloride ion exactly equivalent to the amount of potassium ion liberated in the reaction by the potassium carbonates during the effervescent reaction. The stoichoimetric amount of basic amino acid hydrochloride, i.e., hydrochloride salt of a basic amino acid, required is readily calculated from the amount of potassium carbonates present in the potassium chloride effervescent composition. The basic amino acid hydrochlorides, include lysine hydrochloride, arginine hydrochloride, and histidine hydrochloride, but the preferred amino acid hydrochloride is L-lysine hydrochloride.

The amount of amino acid hydrochloride used in the present composition will generally be in the range of 800 3,000 milligrams.

The potassium carbonate or bicarbonate and the substance which on dissolution in water forms an acid reacting solution may, for example, be a solid, preferably poly-basic organic acid, e.g., tartaric acid or citric acid. The effervescent agent may include some sodium carbonate or bicarbonate, if desired, in addition to the potassium carbonate and bicarbonate. Preferably, the ratio of acid reacting substance to carbonates is in the range of about 1.1 to 1.

The quantity of effervescent agent in each unit of the composition of this invention will vary with the amount of potassium chloride and with the other components of the composition. However, in order to produce a drink resulting from the dissolution of the unit in water having a pleasant soda-like flavor, each unit must contain at least 1 gram of effervescent agent. The preferred composition contains between 1 to 2 grams of effervescent agent, containing 500 to 1,000 milligrams of potassium carbonate or bicarbonate and 500 to 1,000 milligrams of a substance which on dissolution in water forms an acid reacting solution, 800 to 1,200 milligrams of potassium chloride and 900 to 1,100 milligrams of L-lysine hydrochloride in a ratio of effervescent agent to potassium chloride of about 2 to 1 to 0.6 to 1 by weight.

The composition of this invention also includes in addition to potassium chloride, effervescent agents and amino acid hydrochloride, sufficient amounts of sweeteners and flavoring agents to provide a pleasant effervescent drink when the composition is dissolved in water. The preferred sweeteners are saccharin in amounts between 5 milligrams to 100 milligrams per tablet or sachet, sodium cyclamate in amounts up to 500 milligrams per tablet or sachet or sugar in amounts between 500 milligrams to 6 grams per tablet or sachet. The amount of flavoring present is, of course, adjusted in such a way as to give a satisfactory flavor to the effervescent drink. The preferred flavorings are concentrated orange flavor, lemon and lime flavor, punch flavor, or pineapple flavor or mixtures of these flavorings used in quantities between 5 to 50 milligrams per tablet or sachet.

In addition to the above, various other ingredients are added to the composition of this invention to improve the appearance and production of the finished article, especially tablets, such as tabletting aids, for example, lubricants, such as adipic acid, polyethylene glycol, or stearates and binding agents such as ethyl cellulose or polyvinyl pyrrolidone; inert carriers; dyes and pH buffers, for example, phosphate or citrate. All of these ingredients must, of course, be physiologically acceptable and compatible with potassium chloride, carbonate or bicarbonate and amino acid hydrochloride.

The preparation of the granulation is carried out using conventional techniques employing anhydrous materials where possible and drying all hygroscopic ingredients to a negligible moisture content where necessary. For the composition of this invention, it is preferred that immediately after drying all hygroscopic materials, the ingredients be ground to the desired particle size by standard methods and all ingredients mixed together in a suitable mixer until the required uniformity is obtained.

The compositions of the present invention are conveniently provided in the form of tablets or powder packets. The tablets are preferably made on tabletting equipment of the conventional kind, but having a top and bottom punch with resilient operative face, e.g., a top and bottom punch of metal provided with a disc of resilient plastic or like rubbery material inserted in the face. Where the composition of this invention is provided in the form of a powder packet, the ingredients are mixed together in known manner and the packet manufactured by a conventional procedure which provides packets which are moisture resistant.

The preparation of the granulation and the finished composition is preferably carried out in an atmosphere having a relative humidity of less than about 35%; and the granulation and finished compositions of the invention should be stored under substantially anhydrous conditions, for example, by packaging them in a dry moisture impermeable container.

The amount of potassium chloride to be administered in the form of the above composition will naturally vary. Normally, the compositions of the present invention will be made up in units (e.g., tablets or sachets) containing about 1125 grams of potassium chloride. A suitable composition and range of ingredients according to the invention is a tablet comprising:

| | |
|---|---|
| Amino acid Hydrochloride | 0.800 Gm.–3.000 Gm. |
| Potassium Chloride, U.S.P. | 0.500 Gm.–1.500 Gm. |
| Potassium Bicarbonate, U.S.P. | 0.500 Gm.–2.000 Gm. |
| Citric Acid, U.S.P., Anhydrous | 0.500 Gm.–2.000 Gm. |
| Saccharin, U.S.P. | 0.005 Gm.–0.100 Gm. |
| Polyethylene Glycol-6000 | 0.101 Gm.–0.150 Gm. |
| Color and Flavor | q.s. |

EXAMPLE I

Tablets containing the following amounts of ingredients are prepared in the manner described below:

| | |
|---|---|
| L-lysine hydrochloride | 913 mg. |
| Potassium chloride | 1125 mg. |
| Citric acid | 550 mg. |
| Potassium Bicarbonate | 500 mg. |
| Saccharin | 35 mg. |
| Polyethylene glycol-6000 | 60 mg. |
| Lemon-lime Spralene (Kohnstamm L-1236) | 20 mg. |
| Punch flavor (Firmenich 59.722/AP) | 10 mg. |
| Pineapple Aromalok (Fritzsche 28992) | 5 mg. |

Granular potassium bicarbonate for the desired number of tablets is ground through a number 12 screen and dried at 220°F for about 16 hours to remove any moisture present. It is then mixed with the remaining ingredient using standard techniques and apparatus for about 20 minutes. The granulation is tabletted in a conventional manner using 13/16 inch punches.

When the tablet is added to a glass of water, is disintegrates to yield a pleasant tasting effervescent drink, which contains potassium ion and chloride ion in a solution in which the ratio of potassium ion to chloride ion is 1 to 1.

Similar results ae obtained when the L-lysine hydrochloride above is replaced by an equivalent amount of L-aginine hydrochloride or L-histidine hydrochloride.

What is claimed is:

1. A method of treating potassium depletion which comprises orally administering to a human being in need of said treatment large doses of potassium chloride in a pleasant tasting effervescent drink resulting from the dissolution in water of a stable pharmaceutical composition in unit dosage form comprising from 500 to 1,500 milligrams of potassium chloride, 500 to 2,000 milligrams of potassium carbonate or bicarbonate, 500 to 2,000 milligrams of a substance which on dissolution in water forms an acid reacting solution, and an amount of L-lysine hydrochloride sufficient to provide one chloride ion for each potassium ion formed by the dissolution of the composition in water.

2. A method according to claim 1, which comprises orally administering to a human being in need of said treatment large doses of potassium chloride in a pleasant tasting effervescent drink resulting from the dissolution in water of a stable pharmaceutical composition in unit dosage form comprising from 500 to 1,500 milligrams of potassium chloride, 500 to 2,000 milligrams of potassium carbonate or bicarbonate, 500 to 2,000 milligrams of a substance which on dissolution in water forms an acid reacting solution, and 800 to 3,000 milligrams of L-lysine hydrochloride.

3. A method according to claim 2 in which the stable pharmaceutical composition comprises from 800 to 1,200 milligrams of potassium chloride, an effervescent agent comprising 500 to 1,000 milligrams of potassium carbonate or potassium bicarbonate, and 500 to 1,000 milligrams of a substance which on dissolution in water forms an acid reacting solution, and 900 to 1,100 milligrams of L-lysine hydrochloride in a ratio of effervescent agent to potassium chloride of about 2:1 to 0.6:1 by weight.

4. A method according to claim 3 in which the effervescent agent comprises potassium carbonate or bicarbonate and the substance which on dissolution in water forms an acid reacting substance is a polybasic organic acid.

5. A method according to claim 4 in which the ratio of acid reacting substance to potassium carbonate or bicarbonate is about 1.1 to 1 by weight.

6. A method according to claim 3 in which each unit contains from 5 to 100 milligrams of saccharin.

7. A method according to claim 3 in which each unit contains from 5 to 50 milligrams of flavoring.

8. A method of orally administering large quantities of potassium ions and chloride ions in a 1 to 1 ratio, which comprises administering the ions in a pleasant tasting effervescent drink resulting from the dissolution in water of a stable pharmaceutical composition in unit dosage form comprising from 500 to 1,500 milligrams of potassium chloride, 500 to 2,000 milligrams of potassium carbonate or bicarbonate, 500 to 2,000 milligrams of a substance which on dissolution in water forms an acid reacting solution, and an amount of L-lysine hydrochloride sufficient to provide one chloride ion for each potassium ion liberated by the dissolution in water of the composition.

9. A method according to claim 8, which comprises administering the potassium and chloride ions in a pleasant tasting effervescent drink resulting from the dissolution in water of a stable pharmaceutical composition in unit dosage form comprising from 500 to 1,500 milligrams of potassium chloride, 500 to 2,000 milligrams of potassium carbonate or bicarbonate, 500 to 2,000 milligrams of a substance which on dissolution in water forms an acid reacting solution, and 800 to 3,000 milligrams of L-lysine hydrochloride.

10. A method according to claim 9, in which the stable pharmaceutical composition comprises from 800 to 1,200 milligrams of potassium chloride, an effervescent agent comprising 500 to 1,000 milligrams of potassium carbonate or bicarbonate, and 500 to 1,000 milligrams of a substance which on dissolution in water forms an acid reacting solution, and 900 to 1,100 milligrams of L-lysine hydrochloride in a ratio of effervescent agent to potassium chloride of about 2:1 or 0.6:1 by weight.

11. A method according to claim 10 in which the effervescent agent comprises potassium carbonate or bicarbonate, and the substance which on dissolution in water forms an acid reacting substance is a polybasic organic acid.

12. A method according to claim 11 in which the ratio of acid reacting substance to potassium carbonate or bicarbonate is about 1.1 to 1 by weight.

13. A method according to claim 10 in which each unit contains from 5 to 100 milligrams of saccharin.

14. A method according to claim 10 in which each unit contains from 5 to 50 milligrams of flavoring.

15. A stable effervescent potassium chloride composition for oral administration in a pleasant tasting effervescent drink form comprising in unit dosage form 500 to 1,500 milligrams of potassium chloride, 500 to 2,000 milligrams of potassium carbonate or bicarbonate, 500 to 2,000 milligrams of a substance which on dissolution in water forms an acid reacting solution, and an amount of L-lysine hydrochloride sufficient to provide one chloride ion for each potassium ion present in the potassium carbonate or bicarbonate.

16. A stable effervescent potassium chloride composition according to claim 15, comprising in unit dosage form 500 to 1,500 milligrams of potassium chloride, 500 to 2,000 milligrams of potassium carbonate or bicarbonate, 500 to 2,000 milligrams of a substance which on dissolution in water forms an acid reacting solution, and 800 to 3,000 milligrams of L-lysine hydrochloride.

17. A stable effervescent composition according to claim 16, in unit dosage form, containing from 800 to 1,200 milligrams of potassium chloride, 500 to 1,000 milligrams of potassium carbonate or bicarbonate, 500 to 1,000 milligrams of a substance which on dissolution in water forms an acid reacting solution and 900 to 1,100 milligrams of L-lysine hydrochloride.

18. A composition according to claim 16, wherein the effervescent agent comprises potassium carbonate or bicarbonate, and the substance which on dissolution in water forms an acid reacting substance is a polybasic organic acid.

19. A composition according to claim 18, wherein the effervescent agent comprises citric acid or tartaric acid together with potassium carbonate or bicarbonate.

20. A composition according to claim 18, wherein the ratio of acid reacting substance to potassium carbonate or bicarbonate is about 1.1 to 1 by weight.

21. A composition according to claim 16, in the form of a tablet or sachet containing 5 to 100 milligrams of saccharin and 5 to 50 milligrams of flavoring.

22. A composition according to claim 15, which is in the form of a tablet.

* * * * *